United States Patent
Harashima et al.

(10) Patent No.: US 10,485,874 B2
(45) Date of Patent: Nov. 26, 2019

(54) HYALURONIC ACID MODIFIED BY SPHINGOSINE-1-PHOSPHORIC ACID

(71) Applicants: Kewpie Corporation, Tokyo (JP); University of Tsukuba, Tsukuba-shi (JP)

(72) Inventors: Hideyoshi Harashima, Sapporo (JP); Mamoru Hyodo, Sapporo (JP); Naoyuki Toriyabe, Sapporo (JP); Nobuhiro Ohkohchi, Tsukuba (JP); Takafumi Tamura, Tsukuba (JP); Naoki Sano, Tsukuba (JP)

(73) Assignees: Kewpie Corporation, Tokyo (JP); University of Tsukuba, Tsukuba-shi (JP)

( * ) Notice: Subject to any disclaimer, the term of this patent is extended or adjusted under 35 U.S.C. 154(b) by 0 days.

(21) Appl. No.: 15/123,359

(22) PCT Filed: Mar. 5, 2015

(86) PCT No.: PCT/JP2015/056448
§ 371 (c)(1),
(2) Date: Sep. 2, 2016

(87) PCT Pub. No.: WO2015/133559
PCT Pub. Date: Sep. 11, 2015

(65) Prior Publication Data
US 2017/0056509 A1    Mar. 2, 2017

(30) Foreign Application Priority Data

Mar. 6, 2014   (JP) .................................. 2014-043549
Jun. 11, 2014  (JP) .................................. 2014-120485

(51) Int. Cl.
| | |
|---|---|
| *A61K 47/61* | (2017.01) |
| *A61K 47/36* | (2006.01) |
| *A61K 31/661* | (2006.01) |
| *C08B 37/08* | (2006.01) |
| *C08L 5/08* | (2006.01) |
| *A61K 9/00* | (2006.01) |

(52) U.S. Cl.
CPC ............ *A61K 47/36* (2013.01); *A61K 9/0019* (2013.01); *A61K 31/661* (2013.01); *A61K 47/61* (2017.08); *C08B 37/0072* (2013.01); *C08L 5/08* (2013.01)

(58) Field of Classification Search
None
See application file for complete search history.

(56) References Cited

U.S. PATENT DOCUMENTS

| | | | |
|---|---|---|---|
| 7,034,006 B2 * | 4/2006 | Yedgar | A61K 47/48053 514/42 |
| 2002/0016304 A1 | 2/2002 | Maruyama et al. | |
| 2010/0087370 A1 * | 4/2010 | Jain | A61K 38/043 514/1.1 |

FOREIGN PATENT DOCUMENTS

| | | |
|---|---|---|
| JP | 10-158196 A | 6/1998 |
| JP | 2001081103 A | 3/2001 |

OTHER PUBLICATIONS

Pyne, N. J., & Pyne, S. (2010). Sphingosine 1-phosphate and cancer. Nature Reviews Cancer, 10(7), 489-503. (Year: 2010).*
Ohkohchi et al. Research Report, "Development of new reagent for l iver diseases using S1P and hyaluronic acid." retrieved from https://kaken.nii.ac.jp/en/file/KAKENHI-PROJECT-23390319/23390319seika.pdf, on Feb. 13, 2019 (Year: 2011).*
Spot translation of Ohkohchi et al., p. 4, col. 1 bottom, from Stephen Spar in STIC (Year: 2011).*
International Preliminary Report on Patentability dated Sep. 6, 2016 for International Application No. PCT/JP2015/056448, Harashima et al., "Hyaluronic Acid Modified by Sphingosine-1-phosphoric acid," filed Mar. 5, 2015 (8 pages).
International Search Report and Written Opinion dated May 26, 2015 for International Application No. PCT/JP2015/056448, Harashima et al., "Hyaluronic Acid Modified by Sphingosine-1-phosphoric acid," filed Mar. 5, 2015 (14 pages).
Man et al., "FTY720 attenuates hepatic ischemia-reperfusion injury in normal and cirrhotic livers," Am J Transplant. 5(1):40-9 (2005).
Mochizuki et al., "Polysaccharide conjugates as bionanomaterials," Japanese Journal of Polymer Science and Technology. 61(12):601-5 (2004).
Ohkouchi et al., "S1P hyaluronic acid shushoku liposome o mochiita nanjisei kanshogai ni taisuru shinki chiryoyaku no kaihatsu," Kagaku Kenkyuhi Josei Jigyo, Kenkyu Kadai No. 23390319, 2011 to 2013 Nendo, (retrieval date: Apr. 16, 2015) (Abstract Only) (3 pages).
Sano et al., "Hyaluronic acid juyotai o mochiita kan ruido naihi saibo e shuseki suru shinki drug delivery system seizai no kaihatsu," Dai 30 Kai Annual Meeting of the Japan Society of Drug Delivery System Program Yokoshu. 30:169 (Jul. 1, 2014).

(Continued)

*Primary Examiner* — Dale R Miller
(74) *Attorney, Agent, or Firm* — Clark & Elbing LLP; Susan M. Michaud

(57) ABSTRACT

Hyaluronic acid modified with sphingosine-1-phosphate, and a medicine comprising the hyaluronic acid as an active ingredient, wherein the medicine can alleviate hepatic disorder caused by hypoxia/reoxygenation by protecting the liver sinusoidal endothelial cells, and the medicine can prevent and/or treat liver failure due to liver transplantation, hepatectomy, or other surgeries associated with liver ischemia/reperfusion.

5 Claims, 8 Drawing Sheets

(56) References Cited

OTHER PUBLICATIONS

Tamura et al., "Development of a Novel, Sphingosine-1-phosphate loaded, DDS-made Agent for Hepatic Regeneration, Targeted for Liver Sinusoidal Endothelial Cells," Journal of Japan Surgical Society. 114 (special extra issue 2):640 (PS-087-2) (2013) (5 pages).
Zheng et al., "Sphingosine 1-Phosphate protects rat liver sinusoidal endothelial cells from ethanol-induced apoptosis: Role of intracellular calcium and nitric oxide," Hepatology. 44(5):1278-87 (2006).
Extended European Search Report dated Oct. 17, 2017 for European Patent Application No. 15759216.3, Harashima et al., "Hyaluronic Acid Modified by Sphingosine-1-phosphoric acid," filed Mar. 5, 2015 (6 pages).
Office Action dated Oct. 23, 2018 for Japanese Application No. 2016-506542, Hideyoshi et al., "Hyaluronic Acid Modified by Sphingosine-1-Phosphoric Acid," filed Mar. 5, 2015 (20 pages).
Ikeda et al., "Sphingosine 1-phosphate regulates regeneration and fibrosis after liver injury via sphingosine 1-phosphate receptor 2," J Lipid Res. 50(3):556-64 (2009) (9 pages).
Notification of Reasons for Refusal dated Nov. 22, 2018 for Korean Application No. 10-2016-7024519, Hideyoshi et al., "Hyaluronic Acid Modified by Sphingosine-1-Phosphoric Acid," filed Mar. 5, 2015 (10 pages).

\* cited by examiner

ELECTRON MICROSCOPY

HYALURONIC ACID MODIFIED BY SPHINGOSINE-1-PHOSPHORIC ACID

TECHNICAL FIELD

The present invention relates to hyaluronic acid modified with sphingosine-1-phosphate. More specifically, the present invention relates to hyaluronic acid modified with sphingosine-1-phosphate useful as an active ingredient of a medicine for the prevention and/or treatment of hepatic ischemia-reperfusion injury.

BACKGROUND ART

Hypoxia/reoxygenation caused by ischemia/reperfusion is known to be the main cause of postoperative liver failure associated with liver transplantation and hepatectomy. It is also known that protecting liver sinusoidal endothelial cells (LSECs) is important for the prevention of hepatic disorder caused by ischemia/reperfusion (Caldwell et al. Hepatology, 10, pp. 292 to 299, 1989). Based on a report that hypoxia/reoxygenation causes apoptosis in LSECs (Neal R. Banga et al. J. Surg. Res., 178, pp. e35 to 41, 2012), LSECs are considered to be the major factor in hepatic ischemia-reperfusion injury.

Meanwhile, the sphingolipid mediator sphingosine-1-phosphate (S1P) is produced by the phosphorylation of sphingosine derived from sphingomyelin, a component of the cell membrane, by sphingosine kinase. It exhibits a variety of biological activities via S1P receptors. For example, S1P is known to have anti-apoptotic actions (Cuvillier et al., Nature, 381, pp. 800 to 803, 1996), and also reported to inhibit apoptosis in LSECs in alcoholic liver injury (Dong-Mei Zheng et al. Hepatology, 44, pp. 1278 to 1287, 2006) and renal disorder caused by ischemia/reperfusion (Lee et al. Nephrology, 2011).

From the foregoing viewpoints, there is an expectation for the alleviation of hepatic disorder caused by hypoxia/reoxygenation by protecting LSECs with S1P. However, S1P is a metabolite of sphingolipids, which constitute biomembranes, and present in a large amount in platelets and endothelial cells. This poses a problem that S1P itself cannot be used for the prevention and/or treatment of hepatic ischemia-reperfusion injury by targeting LSECs.

In order to solve this problem, there has been an attempt to alleviate hepatic disorder caused by hypoxia/reoxygenation using the S1P receptor agonist FTY720 (fingolimod hydrochloride: converted to phosphorylated FTY720 in vivo by sphingosine kinase) (American Journal of Transplantation, 5, pp. 40 to 49, 2005). However, there is concern that this compound functions as an S1P antagonist in prolonged administration. Also, although this compound has a chemical structure similar to that of sphingosine as a whole, it is not a direct derivative of S1P for having a phenylene group in its carbon chain. FTY720 is not a compound intended to be used for enabling the application of S1P itself to the protection of LSECs.

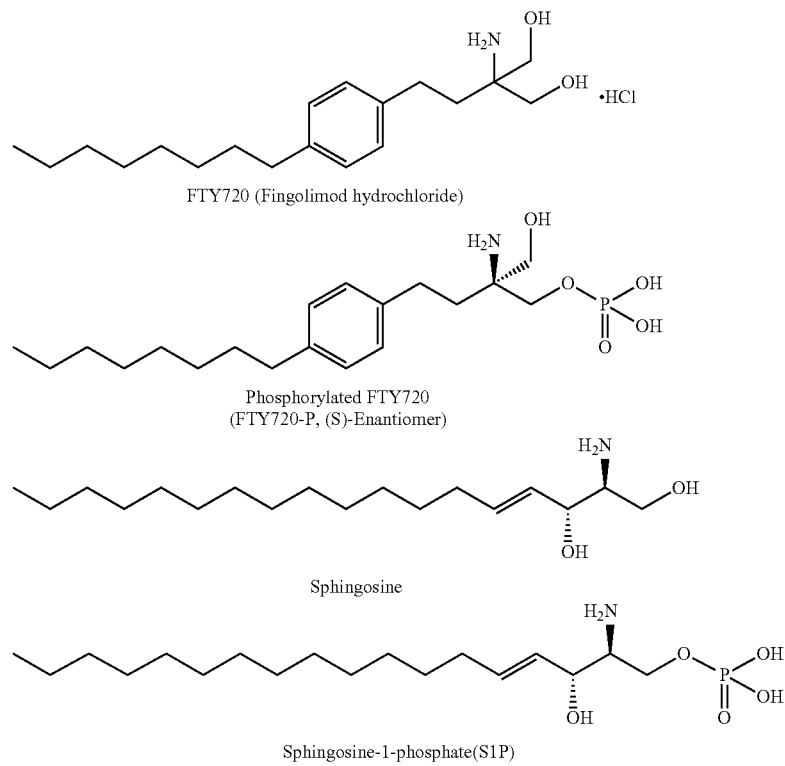

[Chemical Formula 1]

FTY720 (Fingolimod hydrochloride)

Phosphorylated FTY720
(FTY720-P, (S)-Enantiomer)

Sphingosine

Sphingosine-1-phosphate(S1P)

Further, in view of reports that hyaluronic acid (HA) accumulates in LSECs after intravascular administration (Fraser J et al. Cell Tissue Res., 242, pp. 505 to 510, 1985) and the hyaluronic acid receptor (HARE/Stabilin-2) is expressed specifically in LSECs (Bin Zhou et al. J. Biol. Chem., 275, pp. 37733 to 37741, 2000), there has been an attempt to efficiently deliver S1P to LSECs by incorporating S1P in hyaluronic acid-coated liposomes (Grants-in-Aid for Scientific Research, Research Subject No: 23390319, "Development of new reagent for liver diseases using S1P and hyaluronic acid", Nobuhiro Ohkohchi et al., 2011 to 2013). However, there was a problem that hyaluronic acid was functionally deficient as a ligand due to the electric charge, the size of the molecular weight, etc. of the liposomes, resulting in a failure in achieving the desired DDS effect.

PRIOR ART REFERENCES

Non Patent Literatures

Non Patent Literature 1: Caldwell et al., Hepatology, 10, pp. 292 to 299, 1989
Non Patent Literature 2: Neal R. Banga et al., J. Surg. Res., 178, pp. e35 to 41, 2012
Non Patent Literature 3: Cuvillier et al., Nature, 381, pp. 800 to 803, 1996
Non Patent Literature 4: Dong-Mei Zheng et al., Hepatology, 44, pp. 1278 to 1287, 2006
Non Patent Literature 5: Lee et al., Nephrology, 16, pp. 163 to 173, 2011
Non Patent Literature 6: American Journal of Transplantation, 5, pp. 40 to 49, 2005
Non Patent Literature 7: Fraser J et al. Cell Tissue Res., 242, pp. 505 to 510, 1985
Non Patent Literature 8: Grants-in-Aid for Scientific Research, Research Subject No: 23390319, "Development of new reagent for liver diseases using S1P and hyaluronic acid", Nobuhiro Ohkohchi et al., 2011 to 2013 (The Japan Surgical Society Meeting 2013: Development of a novel DDS preparation containing Sphingosine-1-phosphate for liver regeneration, targeting liver sinusoidal endothelial cells)

SUMMARY OF INVENTION

Problems to be Solved by the Invention

The present invention aims to provide a substance capable of alleviating hepatic disorder caused by hypoxia/reoxygenation by protecting LSECs. More specifically, an object of the present invention is to provide a substance capable of alleviating hepatic disorder caused by hypoxia/reoxygenation, wherein the substance protects LSECs by exhibiting its anti-apoptotic actions by efficiently accumulating in LSECs following administration through a form such as intravenous administration.

Means to Solve the Problems

The present inventors conducted intensive research in order to solve the aforementioned problem. As a result, they found that hyaluronic acid modified with S1P accumulates in LSECs with extreme efficiency and the modified hyaluronic acid is highly effective for the inhibition of apoptosis in LSECs due to hypoxia/reoxygenation. They further found that hepatic disorder caused by hypoxia/reoxygenation can be efficiently prevented and/or treated by administering the hyaluronic acid modified with S1P to mammals including humans via an administration route such as intravenous administration. The present invention was completed based on these findings.

That is, the present invention provides hyaluronic acid modified with sphingosine-1-phosphate. The above hyaluronic acid is obtainable by covalently binding sphingosine-1-phosphate to hyaluronic acid.

According to a preferred embodiment of the invention, hyaluronic acid modified with sphingosine-1-phosphate is provided, which is obtainable by condensing hyaluronic acid and sphingosine-1-phosphate. The above hyaluronic acid can be obtained preferably by forming an amide bond between the carboxyl group of hyaluronic acid and the amino group of sphingosine-1-phosphate.

From another viewpoint, the present invention provides a medicine for the prevention and/or treatment of liver failure associated with liver ischemia/reperfusion, wherein the medicine comprises hyaluronic acid modified with sphingosine-1-phosphate as an active ingredient; and a medicine for the prevention and/or treatment of liver failure after liver surgery involving hepatic vascular exclusion, wherein the medicine comprises hyaluronic acid modified with sphingosine-1-phosphate as an active ingredient. Examples of liver surgery involving hepatic vascular exclusion include liver transplantation and partial liver resection.

Further, the present invention provides a medicine for the prevention and/or treatment of liver failure caused by hypoxia/reoxygenation due to liver ischemia/reperfusion, wherein the medicine comprises hyaluronic acid modified with sphingosine-1-phosphate as an active ingredient; and a medicine for the inhibition of apoptosis in liver sinusoidal endothelial cells attributable to hypoxia/reoxygenation caused by liver ischemia/reperfusion, wherein the medicine comprises hyaluronic acid modified with sphingosine-1-phosphate as an active ingredient.

From yet another viewpoint, the present invention provides the use of hyaluronic acid modified with sphingosine-1-phosphate for the production of the aforementioned medicines; a method for the prevention and/or treatment of liver failure associated with liver ischemia/reperfusion, wherein the method comprises the step of administering a preventively and/or therapeutically effective amount of hyaluronic acid modified with sphingosine-1-phosphate to mammals including humans; a method for the prevention and/or treatment of liver failure after liver surgery involving hepatic vascular exclusion, wherein the method comprises the step of administering a preventively and/or therapeutically effective amount of hyaluronic acid modified with sphingosine-1-phosphate to mammals including humans; a method for the prevention and/or treatment of liver failure caused by hypoxia/reoxygenation due to liver ischemia/reperfusion, wherein the method comprises the step of administering a preventively and/or therapeutically effective amount of hyaluronic acid modified with sphingosine-1-phosphate to mammals including humans; a method for the inhibition of apoptosis in liver sinusoidal endothelial cells attributable to hypoxia/reoxygenation caused by liver ischemia/reperfusion, wherein the method comprises the step of administering a preventively and/or therapeutically effective amount of hyaluronic acid modified with sphingosine-1-phosphate to mammals including humans.

Effect of the Invention

The hyaluronic acid modified with sphingosine-1-phosphate provided by the present invention accumulates in liver sinusoidal endothelial cells with extreme efficiency, and is capable of inhibiting apoptosis in liver sinusoidal endothelial cells due to hypoxia/reoxygenation. Further, the medicine containing hyaluronic acid modified with sphingosine-1-phosphate as an active ingredient provided by the present invention is highly effective for the prevention and/or treatment of liver failure caused by hypoxia/reoxygenation associated with liver ischemia/reperfusion, and thus is extremely useful as a medicine for the prevention and/or treatment of liver failure after liver surgery involving hepatic vascular exclusion.

DESCRIPTION OF EMBODIMENTS

Figure 1:
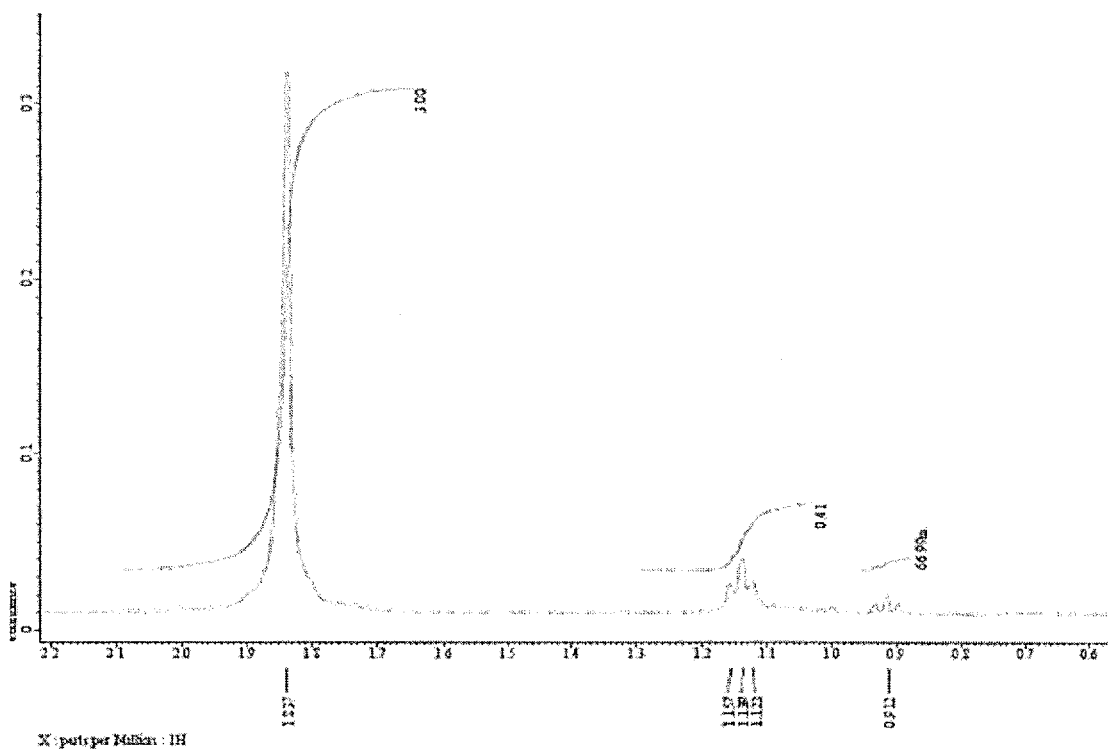
FIG. 1 is an NMR chart of hyaluronic acid modified with sphingosine-1-phosphate synthesized in Example 1 of Examples.

The present invention provides hyaluronic acid modified with sphingosine-1-phosphate (hereinbelow, may be abbreviated as "HA-S1P"). HA-S1P is obtainable by covalently binding sphingosine-1-phosphate to hyaluronic acid. For example, HA-S1P is obtainable by condensing hyaluronic acid and sphingosine-1-phosphate in the presence of a condensing agent. In general, an amide bond may be formed between the carboxyl group of hyaluronic acid and the amino group of sphingosine-1-phosphate by condensation. Having said that, the form of covalent binding of sphingosine-1-phosphate to hyaluronic acid is not limited to the aforementioned amide bond, and it is also possible that the carboxyl group of hyaluronic acid and the hydroxyl group of sphingosine-1-phosphate are linked via an ester bond.

Hyaluronic acid is a polymer of disaccharide units consisting of N-acetylglucosamine and glucuronic acid (each unit has a molecular weight of roughly 400) linked together, which generally has a molecular weight of about 5,000 to 8,000,000. For example, the number of disaccharide units contained in hyaluronic acid with a molecular weight of 600,000 is about 1,500 and the number of disaccharide units contained in hyaluronic acid with a molecular weight of 8,000 is about 20. In general, hyaluronic acid is obtainable as free-form hyaluronic acid or as sodium hyaluronate. The term "hyaluronic acid" as used herein encompasses sodium hyaluronate. Hyaluronic acid or sodium hyaluronate has been provided for use in foods and cosmetics, and has also been used as a medicine.

For example, as sodium hyaluronate used for osteoarthritis, one with a molecular weight of about 600,000 to 1,200,000 (trade name "Artz") and one with a molecular weight of about 500,000 to 730,000 (trade name "Hyalgan") are used, and for ophthalmic surgery, one with a molecular weight of about 600,000 to 1,200,000 (trade name "Opegan"), one with a molecular weight of about 1,900,000 to 3,900,000 (trade name "Opegan Hi"), one with a molecular weight of about 1,900,000 to 3,900,000 (trade name "Hyarone"), and one with a molecular weight of about 1,530,000 to 2,130,000 (trade name "Opelead") are used. Further, sodium hyaluronate with a low molecular weight of about 10,000 to 100,000 as obtained by enzymatic treatment, and further, one with an ultra-low molecular weight of about 500 to 5,000, and the like have also been provided.

The molecular weight of hyaluronic acid used as the raw material to prepare the HA-S1P of the present invention is not particularly limited. In addition to those exemplified above, hyaluronic acids with various molecular weights can be used. For example, hyaluronic acid with an average molecular weight of about 500,000 to 700,000 and hyaluronic acid with an average molecular weight of about 8,000 as obtained by enzymatic treatment can be used as the raw materials. The origin of hyaluronic acid used as the raw material to prepare the hyaluronic acid modified with sphingosine-1-phosphate of the present invention is not particularly limited, and hyaluronic acid derived from any origin such as cockscomb and fermentation can be used.

Although the production method of the HA-S1P of the present invention is not particularly limited, for example, it can be easily produced by condensing hyaluronic acid and sphingosine-1-phosphate in the presence of a condensing agent. The kind of condensing agent is not particular limited, and any condensing agent that can be normally used can be used. For example, a carbodiimide-based condensing agent, an imidazole-based condensing agent, and a triazine-based condensing agent can be used. Examples of the carbodiimide-based condensing agent include N,N'-dicyclohexylcarbodiimide (DCC), N,N'-diisopropylcarbodiimide (DIC), and 1-ethyl-3-(3-dimethylaminopropyl)carbodiimide (EDC) hydrochloride, of which EDC can be particularly preferably used. Along with a condensing agent, for example, N-hydroxysuccinimide (NHS) can also be used as a carboxylic acid-activating agent.

Normally, a condensation reaction can be carried out by adding a condensing gent such as EDC and a carboxylic acid-activating agent such as NHS to hyaluronic acid (free form), followed by the addition of sphingosine-1-phosphate, and then allowing reactions to proceed at room temperature or while heating for about several hours to several days. The reaction can be carried out using about 0.5 to 2 µg of sphingosine-1-phosphate relative to 1 mg of hyaluronic acid. As to the condensing agent, about 1 to 20 mole equivalents, preferably about 10 mole equivalents are used relative to sphingosine-1-phosphate. The reaction can be carried out in a solvent such as water, methanol, ethanol, dimethyl sulfoxide (DMSO), dimethylformamide (DMF), tetrahydrofuran (THF), and dichloromethane or a mixture of these solvents, or without a solvent. Upon completion of the reaction, normally, the desired substance can be obtained by removing EDC, NHS, and unreacted sphingosine-1-phosphate by means of, for example, dialysis. Normally, the binding of sphingosine-1-phosphate to hyaluronic acid can be confirmed by NMR. In general, hyaluronic acid modified with sphingosine-1-phosphate in which about 10 to 50%, preferably about 12 to 40% of the total number of carboxylic acid groups in one hyaluronic acid molecule are bound to the amine of sphingosine-1-phosphate may be prepared. The number of sphingosine-1-phosphate moieties bound to one hyaluronic acid molecule can be computationally determined by, for example, obtaining an integrated value from the N-acetyl group (1.8 ppm) of hyaluronic acid and the terminal methyl group and methylene group (0.9 ppm and 1.1 ppm) in the lipid moiety of sphingosine-1-phosphate by proton NMR.

The HA-S1P provided by the present invention can efficiently accumulate in liver sinusoidal endothelial cells and inhibit apoptosis in liver sinusoidal endothelial cells due to hypoxia/reoxygenation; therefore, a medicine containing HA-S1P as an active ingredient is useful as a medicine for the prevention and/or treatment of liver failure associated with liver ischemia/reperfusion. Although the kind of procedure or treatment that causes liver ischemia/reperfusion is not particularly limited, the representative procedure may be, for example, liver surgery involving hepatic vascular exclusion. Examples of such liver surgery include, but are not limited to, liver transplantation and partial liver resection; however, any surgery involving temporarily clamping a blood vessel leading to liver with a clip, and about several minutes to 15 minute later, unclamping to restart blood flow can be the indication for the medicine of the present invention. While not wishing to be bound by any theory, in liver failure caused by hypoxia/reoxygenation due to liver ischemia/reperfusion, apoptosis in liver sinusoidal endothelial cells attributable to hypoxia/reoxygenation occurs, and the medicine of the present invention has an inhibitory action on such apoptosis.

Generally, the medicine of the present invention can be administered to mammals including humans by parenteral administration such as intravenous administration and intraperitoneal administration. When intravenous administration is given, an ordinary means such as intravenous injection and drip infusion can be adopted. Alternatively, it is also possible to intravascularly administer the medicine of the present invention through the portal vein during surgery. When low molecular weight hyaluronic acid is used, it may be administered orally in the form of, for example, liquids and capsules. Although the administration is desirably given from about several minutes to one hour before vascular exclusion, for example, during a time period between about 10 minutes to 30 minutes before vascular exclusion, the timing of administration is not limited as long as it is before vascular exclusion. In the case of liver transplantation, the medicine of the present invention can be administered to the donor during the resection of a portion of the liver in such a manner that an adequate amount of the medicine of the present invention remains in the liver, while the medicine of the present invention can also be administered to the recipient patient immediately before transplantation. However, such a method of administration as mentioned above can be selected as appropriate, and a method of administration is not limited to any specific aspect.

The medicine of the present invention is normally provided as an injection or a drip in the form of an aqueous solution or a freeze-dried product. In preparing formulations, a formulation additive normally used for the production of injections and drips can be employed. For example, a pH modulator, a stabilizer, a buffer, or the like can be used for aqueous solutions, and for freeze-dried formulations, in addition to those mentioned above, a solubilizer and the like can be used. However, the formulation additive is not limited to those specified above, and those skilled in the art can select an appropriate formulation additive according to their purposes.

EXAMPLES

Hereinbelow, the present invention will be more specifically described with reference to Examples; however, the scope of the present invention is not limited by the following Examples.

Example 1: Synthesis of HA-S1P

To 5 ml of hyaluronic acid (2 mg/ml, one with a molecular weight of 600,000 or one with a molecular weight of 8,000), 95.85 μl of EDC (100 mg/ml) and 57.535 μl of NHS (100 mg/ml) were added, followed by thorough mixing. To the resulting mixture, 67.378 μl of S1P (25 mg/ml) was added, followed by stirring at 55° C., and reactions were allowed to proceed for 24 hours. Then, EDC, NHS, and unbound S1P were removed by dialysis. The introduction of S1P was confirmed by the presence of a peak near 1.15 ppm by measuring NMR (FIG. 1). The amount of S1P bound to the carboxylic acid of the hyaluronic acid accounted for 13.5 to 40%.

Example 2

(1) Method
Animals
Male Sprague-Dawley (hereinbelow, SD) rats, 200 to 250 g, were obtained from CLEA Japan, Inc. (Tokyo, Japan). Four groups of SD rats were studied.
A study was conducted for a methanol-administration group, where methanol was the solvent for S1P (the content of administration:methanol (50 μl)+3% BSA (150 μl), 200 μl in total), a HA-administration group (the content of administration: 8 kDa HA dissolved in methanol:ultrapure water=1:3 at 0.32564 g/l, 200 μl in total), an S1P-administration group (the content of administration: 100 μg/kg in terms of the dose of S1P, S1P (50 μl)+3% BSA (150 μl), 200 μl in total), a HA-S1P-administration group (the content of administration: 100 μg/kg in terms of the dose of S1P, the HA-S1P formulation prepared at Hokkaido University was dissolved in methanol:ultrapure water=1:3 at 0.358 g/l, 200 μl in total).
All the procedures used in the animal experiments were in accordance with the standards set forth in a guideline for the handling and use of animal experiments issued by Tsukuba University.
Liver Ischemia Model
Each agent was injected into the tail vein of rats. Ten minutes after the injection, the hepatic artery, portal vein, and bile duct were occluded at once with microclips for 20 minutes. Upon completion of 20 minutes of total liver ischemia, the occlusion was released. For pathological examination, liver tissues were removed from 10 to 15 rats in each group 120 minutes after reperfusion. Also, blood was collected immediately before the injection of the agents and 30 minutes, 60 minutes, and 120 minutes after reperfusion.
Adjustment of Tissues
The liver tissues were fixed in 10% buffered formalin, and then embedded in paraffin, followed by staining with hematoxylin and eosin. The tissue sections of each group were evaluated. The sinusoid structure was observed in a middle-magnification field (200×), in which the portal vein and central vein were shown in the same view.

Immunohistochemical Study

Using DeadEnd® Colorimetric TUNEL System (G7360) supplied by Promega KK, apoptosis-positive cells were immunohistochemically detected. The tissue sections of each group were evaluated. The number of TUNEL-positive cells and the total number of hepatocytes were counted in 10 randomly selected high-power fields (400×) focusing on the portal vein. The results thus obtained were shown as the ratio of TUNLE-positive cell count/total hepatocyte count and compared among the groups.

Protein Extraction and Western Blot Analysis

The liver tissues were stored at −80° C., and then homogenized in 150 mmol/L NaCl, 50 mM TrisCl, 1% NP-40, and a protease inhibitor. The resulting samples were centrifuged and supernatants were collected for analysis. The samples thus obtained were separated by electrophoresis using 12% dodecyl sulfate and polyacrylamide gel, and then transferred to nitrocellulose membranes (Millipore, Bedford, Mass., USA). As the primary antibody, anti-cleaved caspase 3 antibody (9661) and HO-1 antibody (5141) (Cell Signaling Technology, Beverly, Mass., USA) were used. As the secondary antibody, anti-rabbit IgG, HRP linked (7074) (Cell Signaling Technology, Beverly, Mass., USA) was used.

Biochemical Analysis

In order to evaluate the injury of liver parenchyma, the serum ALT value was measured with an autoanalyzer (FUJI DRI-CHEM 7000V, Fujifilm, Tokyo, Japan).

Electron Microscopy

The liver sinusoidal endothelial cells after ischemia/reperfusion were evaluated with an electron microscopy. The liver was quickly excised 120 minutes after reperfusion. Samples removed from the left lobe of the liver were cut into a size of 1 mm$^3$ and stored in 2.5% glutaraldehyde. For postfixation, 1% osmium tetraoxide was used. Subsequently, the samples were brought into contact with alcohols of different concentrations in a stepwise manner for dehydration, and then embedded in Epon. Ultra-thin sections were produced with Ultracut S microtome (Leica Aktiengesellschaft, Vienna, Austria) using a copper grid. In order to enhance contrast, the sections thus obtained were adjusted with uranyl acetate and brought into contact with citrate. The resulting specimens were observed with Hitachi H-7000 transmission electron microscopy (Hitachi, Ltd., Tokyo, Japan).

Statistical Analysis

Statistical analysis was conducted using the Kruskal Wallis H-test and the Mann-Whitney U test with Bonferroni correction as a post hoc test. Also, p< 0.05 was accepted to be indicative of statistical significance.

(2) Experimental System

Figure 2:
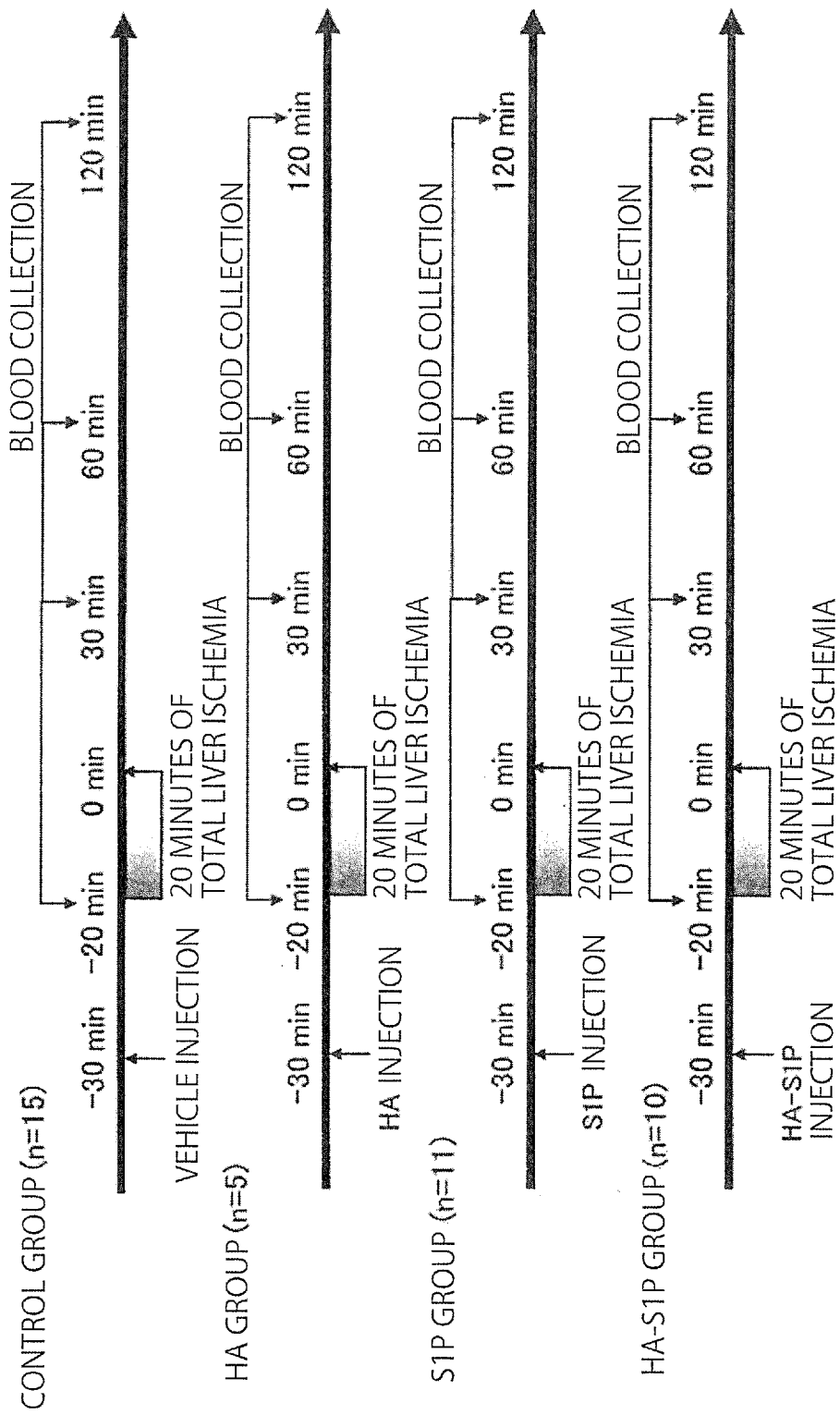
FIG. 2 is a set of diagrams illustrating the experimental procedure carried out in four groups in Example 2 of Examples.

Using 200 to 250 g SD rats, four experimental groups (A) to (D) were prepared. (A) A vehicle group receiving only methanol, the solvent for S1P (methanol (50 µl)+3% BSA (150 µl), 200 µl in total), (B) a HA group receiving only hyaluronic acid (8000 kDa hyaluronic acid dissolved in methanol:ultrapure water=1:3 at 0.32564 g/l, 200 µl in total), (C) a S1P group receiving only S1P (100 µg/kg in terms of the dose of S1P, S1P dissolved in methanol (50 µl)+3% BSA (150 µl), 200 µl in total), and (D) a HA-S1P group (100 µg/kg in terms of the dose of S1P, HA-S1P dissolved in methanol:ultrapure water=1:3 at 0.358 g/L, 200 µl in total). The rats were put under general anesthesia with somnopentyl and isoflurane, and after collecting blood, each of the agents was administered via the tail vein. The rats were subjected to a laparotomy, and 10 minutes after the administration of the agents, total liver ischemia was performed for 20 minutes with microclips. Twenty minutes later, the clips were removed to allow reperfusion, and blood was collected 30 minutes, 60 minutes, and 120 minutes after reperfusion. After 120 minutes, the rats were sacrificed and liver tissues (left lobes) were collected. The experimental procedure is shown in FIG. 2.

(3) Measurement of Liver Function (ALT)

Figure 3:
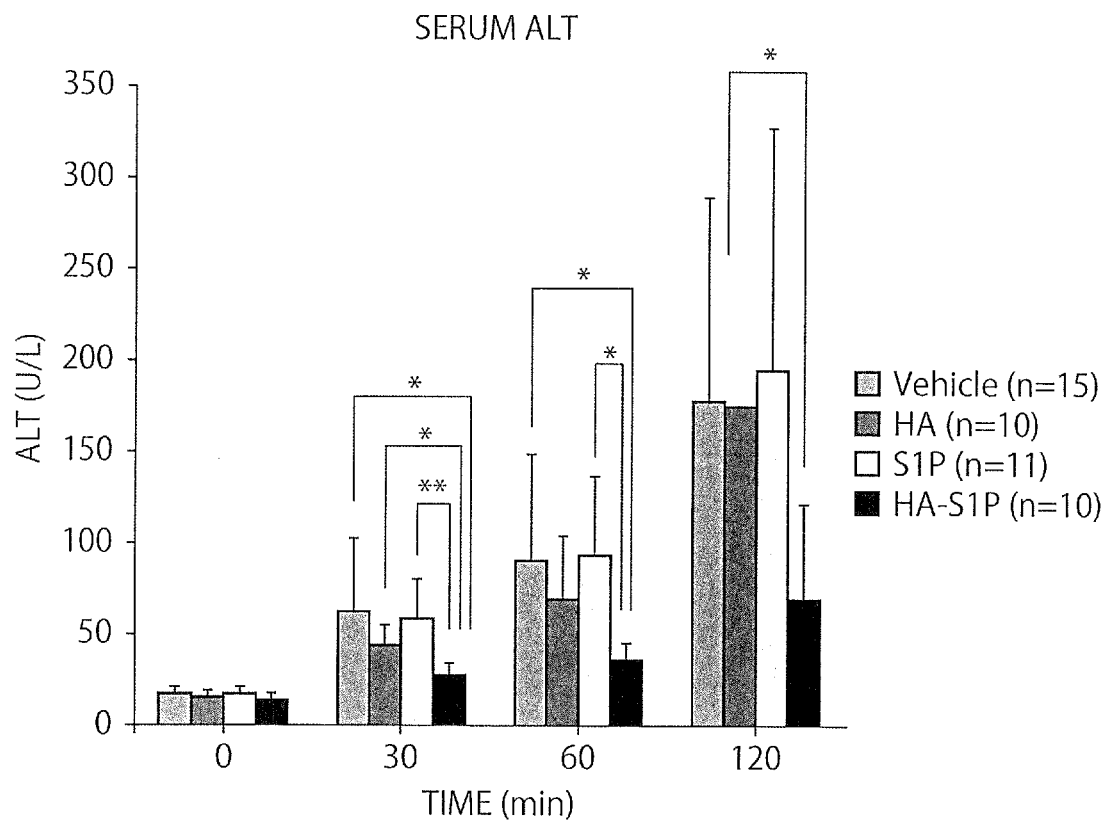
FIG. 3 is a graph showing the results of the measurement of liver function (ALT).

The HA-S1P group showed a significantly lower serum ALT value than the vehicle and S1P groups 30 minutes after reperfusion. The HA-S1P group showed a significantly lower value than the vehicle, HA, and S1P groups 60 minutes after reperfusion. The HA-S1P group showed a significantly lower value than the HA group 120 minutes after reperfusion. The results are shown in FIG. 3.

(3) Confirmation of Apoptosis and Liver-Protecting Action by Western Blot

Figure 4:
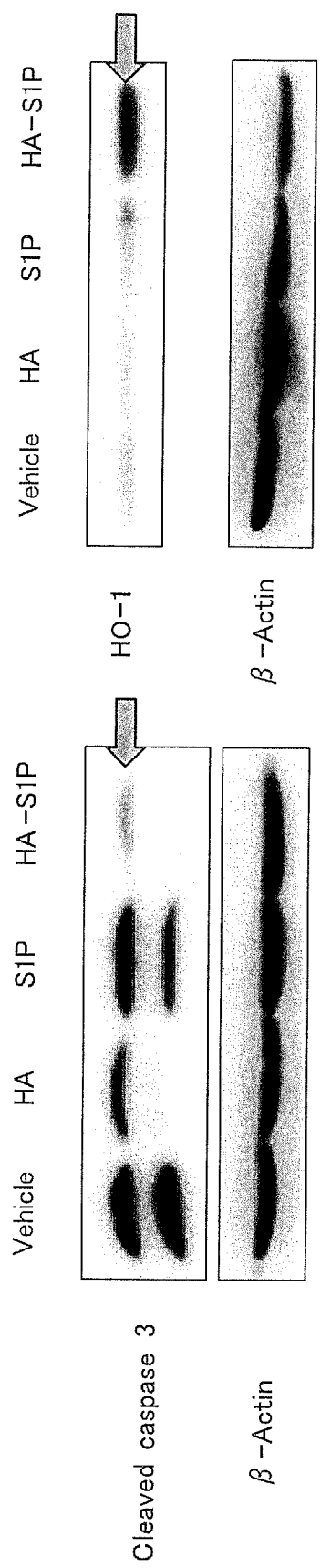
FIG. 4 is a set of diagrams showing the results of the confirmation of the expression of cleaved caspase 3 by Western blot.

As a result of confirming the expression of the apoptosis-related protein cleaved caspase 3 by Western blot in accordance with the method described in a literature (Tamura et al., J Surg Res, 178, pp. 443 to 451, 2012), the expression was inhibited only in the HA-S1P group, suggesting that apoptosis was significantly inhibited in the HA-S1P group. Also, the expression of HO-1, which has a liver-protecting action, was increased only in the HA-S1P group. The results are show in FIG. 4.

(4) Pathological Evaluation of Liver

Figure 5:
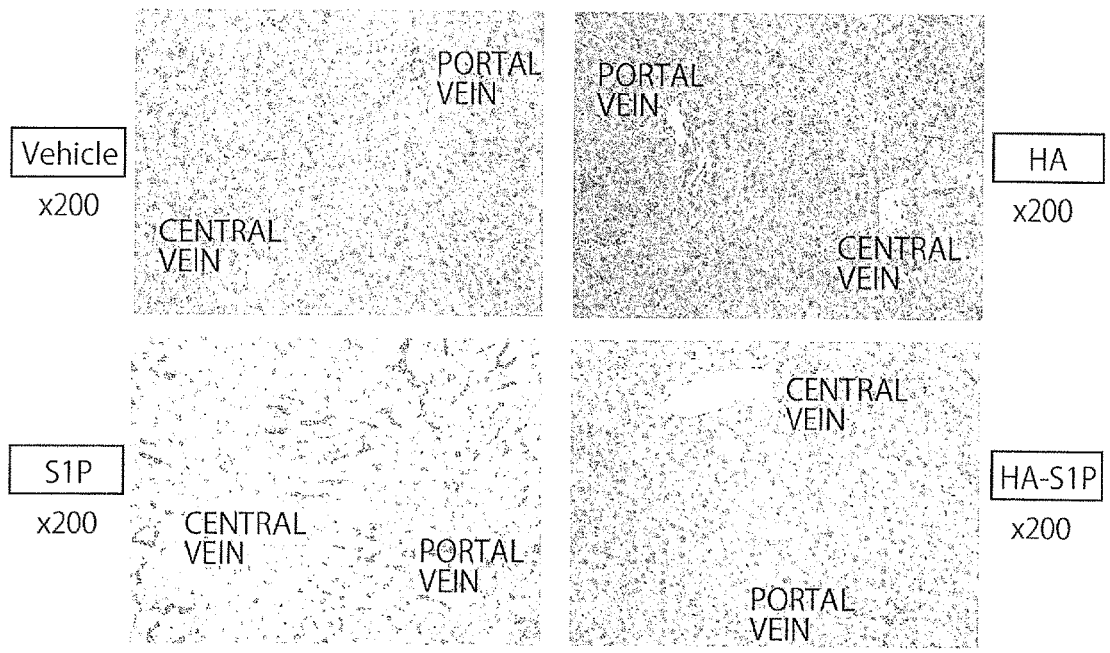
FIG. 5 is a set of diagrams showing the results of HE staining as the pathological evaluation of liver.
Figure 6:
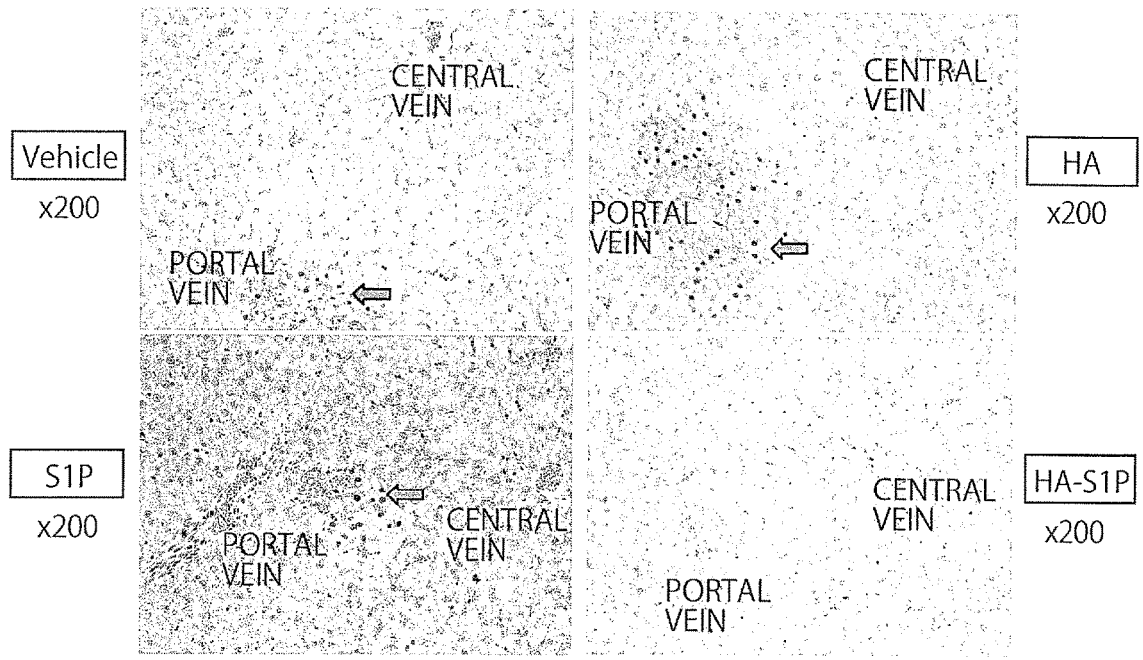
FIG. 6 is a set of diagrams showing the results of TUNEL staining as the pathological evaluation of liver.
Figure 7:
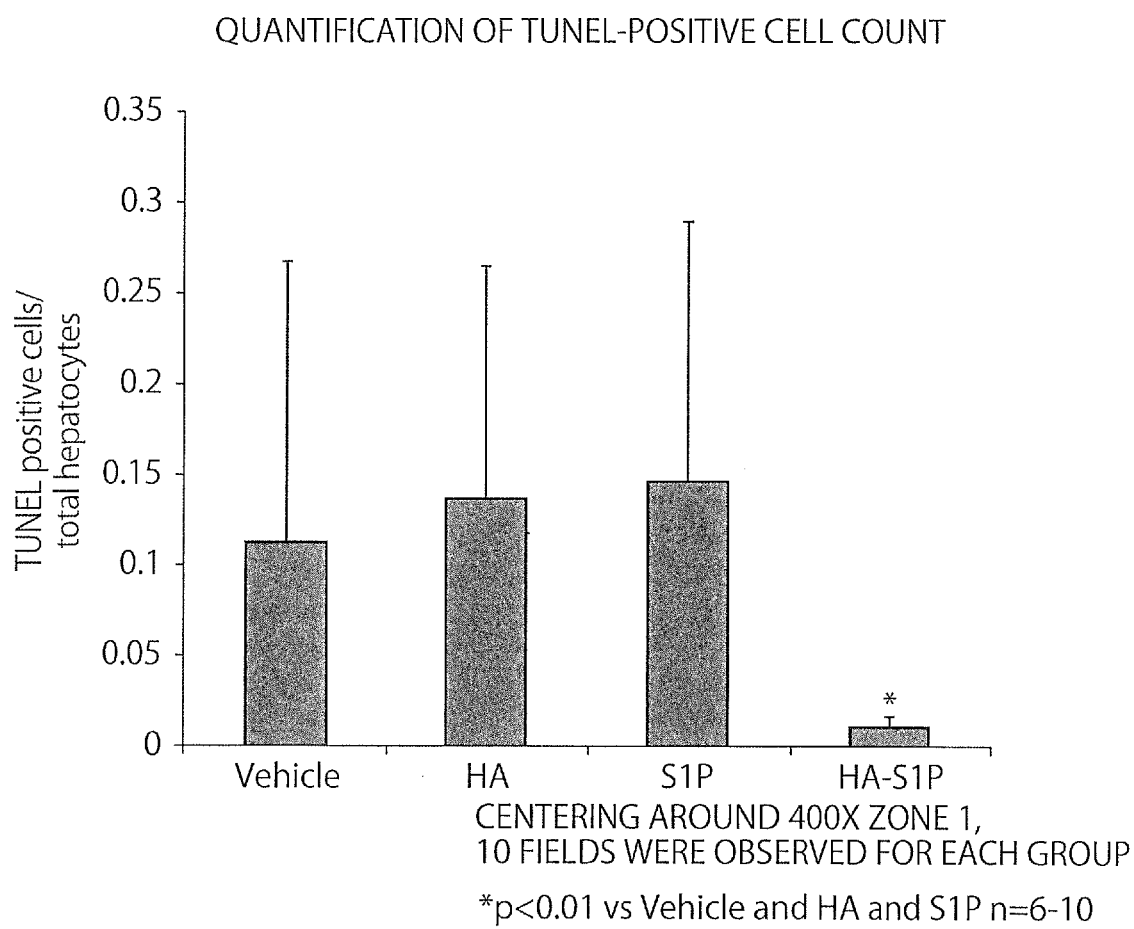
FIG. 7 is a graph showing the results of the quantification of the number of cells that indicated a request by TUNEL staining.

HE staining revealed that the sinusoid structure was maintained in HA-S1P, whereas the narrowing and winding of sinusoid were observed in the other groups (FIG. 5). In TUNEL staining, positive cells were almost unobserved in the HA-S1P group, whereas they were observed mainly in Zone 1 near the portal vein, the site known to be prone to ischemia/reperfusion injury, in the other groups (FIG. 6). Also, as a result of quantification by counting the number of TUNEL-positive cells/the total number of hepatocytes in 400× fields, centering around Zone 1, per 10 fields for each TUNEL staining sample, the percentage of TUNEL-positive cells was significantly low in the HA-S1P group (FIG. 7).

(5) Electron Microscopic Evaluation of the Microstructure of Liver

Figure 8:
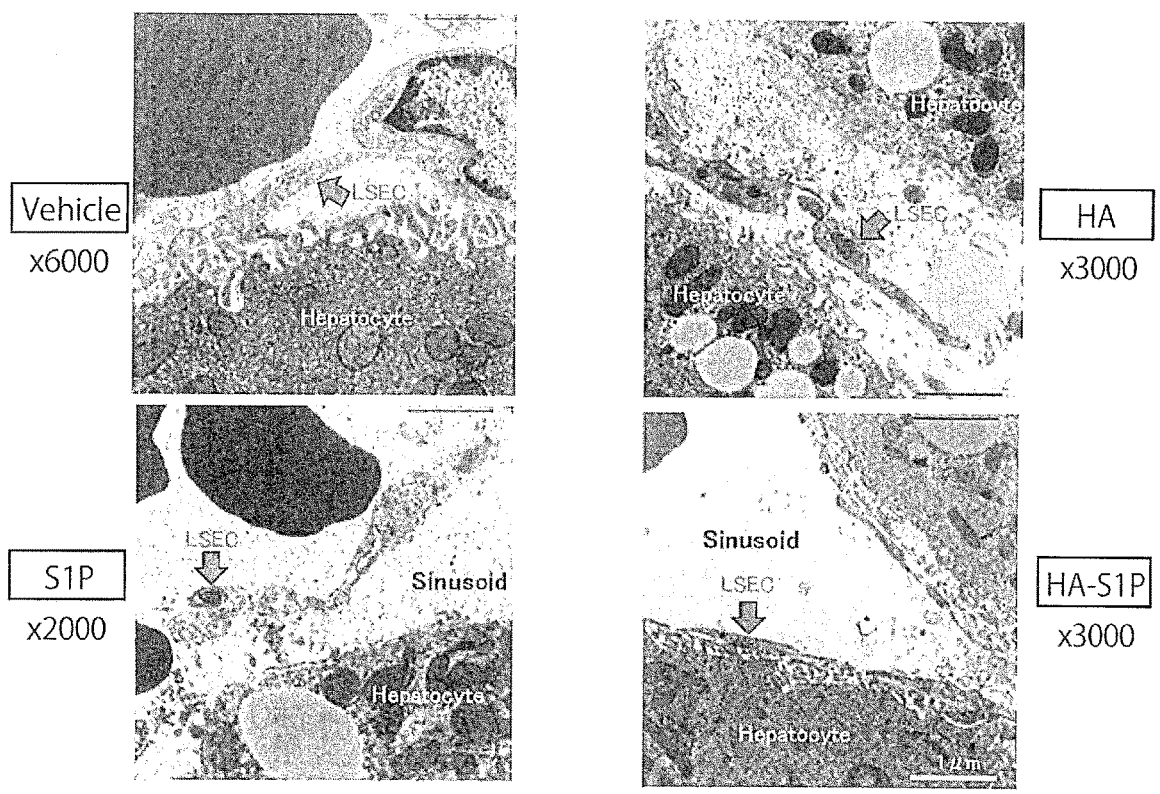
FIG. 8 is a set of diagrams showing the results of the electron microscopic evaluation of the microstructure of liver.

Electron microscopic images confirmed that the undercoat structure of LSECs was maintained in the HA-S1P group, whereas LSECs were injured and came loose in the sinusoid in the other groups (FIG. 8).

Example 3: Confirmation of the Accumulation of S1P in the Liver by Western Blot

The expression of S1P in the liver tissues was confirmed by Western blot in accordance with the following method.

The rat liver tissues stored at −80° C. were homogenized in a buffer prepared from various reagents (150 mmol/L NaCl, 50 mM Tris-Cl, 1% NP-40, and a protease inhibitor). The resulting samples were centrifuged and the supernatants were collected for analysis. The samples thus obtained were separated using 10% SDS-PAGE gel and transferred to nitrocellulose membranes (Millipore, Bedford, Mass.). As the primary antibody, Anti-S1P antibody (ab140592) (1:1000, rabbit polyclonal, Abcam, Cambridge, UK) was used. As the secondary antibody, Anti-rabbit IgG, HRP-linked antibody (#7074S) (1:1000, Cell Signalling Technology, Beverley, Mass., USA) was used.

Figure 9:
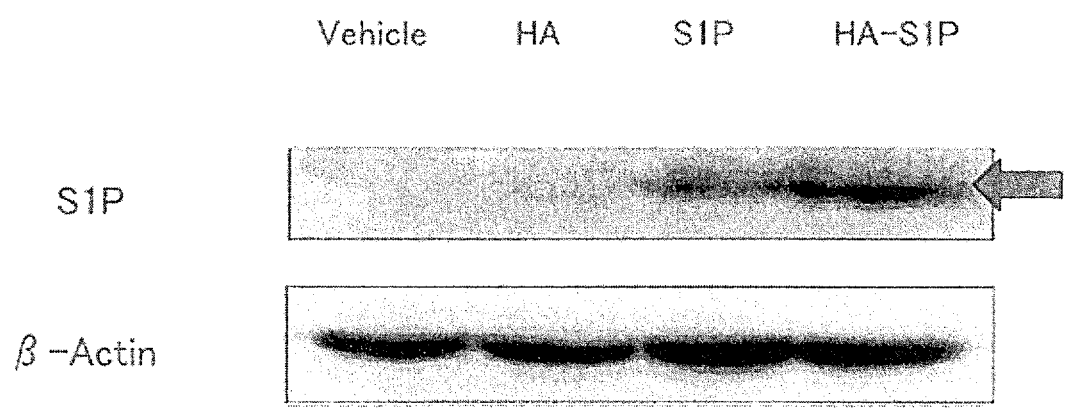
FIG. 9 is a set of diagrams showing the results of the confirmation of the accumulation of S1P in the liver by Western blot.

The results are shown in FIG. 9. The expression of S1P was higher in the HA-S1P sample than in the S1P only sample, suggesting that more specific accumulation in the liver was achieved with HA-S1P than with only S1P.

The invention claimed is:

1. A method for the treatment of liver failure associated with liver ischemia/reperfusion in a subject, the method comprising administering to the subject hyaluronic acid modified with sphingosine-1-phosphate as an active ingredient, wherein the hyaluronic acid modified with sphingosine-1-phosphate is obtainable by covalently binding sphingosine-1-phosphate to hyaluronic acid.

2. A method for the treatment of liver failure after liver surgery involving hepatic vascular exclusion in a subject, the method comprising administering to the subject hyaluronic acid modified with sphingosine-1-phosphate as an active ingredient, wherein the hyaluronic acid modified with sphingosine-1-phosphate is obtainable by covalently binding sphingosine-1-phosphate to hyaluronic acid.

3. The method according to claim 2, wherein the liver surgery involving hepatic vascular exclusion is liver transplantation and partial liver resection.

4. A method for the treatment of liver failure attributable to hypoxia/reoxygenation due to liver ischemia/reperfusion in a subject, the method comprising administering to the subject hyaluronic acid modified with sphingosine-1-phosphate as an active ingredient, wherein the hyaluronic acid modified with sphingosine-1-phosphate is obtainable by covalently binding sphingosine-1-phosphate to hyaluronic acid.

5. A method for the inhibition of apoptosis in liver sinusoidal endothelial cells attributable to hypoxia/reoxygenation caused by liver ischemia/reperfusion in a subject, the method comprising administering to the subject hyaluronic acid modified with sphingosine-1-phosphate as an active ingredient, wherein the hyaluronic acid modified with sphingosine-1-phosphate is obtainable by covalently binding sphingosine-1-phosphate to hyaluronic acid.

* * * * *